United States Patent
Johnson et al.

[11] Patent Number: 6,080,185
[45] Date of Patent: Jun. 27, 2000

[54] STOP MECHANISM AND METHOD THEREFOR

[75] Inventors: Greg A. Johnson; James A. Magovern, both of Pittsburgh, Pa.; Eric LaWhite, South Royalton, Vt.; Wayne P. Griffin, Cranberry, Pa.

[73] Assignee: Cardiac Assist Technologies, Inc., Pittsburgh, Pa.

[21] Appl. No.: 09/173,890

[22] Filed: Oct. 16, 1998

[51] Int. Cl.$^7$ ...................................................... A61B 17/04
[52] U.S. Cl. ........................... 606/233; 606/96; 606/103; 606/151; 606/232; 606/185
[58] Field of Search .................................. 606/80, 83, 96, 606/184, 185, 188, 213, 215, 216, 219, 221, 232, 233, 151, 103; 128/898

[56] References Cited

U.S. PATENT DOCUMENTS

| | | |
|---|---|---|
| 4,279,248 | 7/1981 | Gabbay . |
| 4,532,926 | 8/1985 | O'Holla . |
| 4,730,615 | 3/1988 | Sutherland et al. . |
| 4,750,492 | 6/1988 | Jacobs . |
| 4,802,477 | 2/1989 | Gabbay . |
| 5,139,498 | 8/1992 | Astudillo Ley . |
| 5,356,412 | 10/1994 | Golds et al. . |
| 5,366,461 | 11/1994 | Blasnik . |
| 5,437,685 | 8/1995 | Blasnik . |
| 5,462,542 | 10/1995 | Alesi, Jr. . |
| 5,584,835 | 12/1996 | Greenfield . |
| 5,720,747 | 2/1998 | Burke . |
| 5,720,765 | 2/1998 | Thal . |
| 5,810,826 | 9/1998 | Akerfeldt et al. . |
| 5,814,071 | 9/1998 | McDevitt et al. . |
| 5,814,073 | 9/1998 | Bonutti . |
| 5,849,004 | 12/1998 | Bramlet . |

OTHER PUBLICATIONS

R. Labitzke, G. Schrammt, U. Witzel, and P. Quisthout, "Sleeve–Rope Closure" of the Median Sternotomy after Open Heart Operations, Thorac, cardiovasc, Surgeon 31 (1983) 127–128, Georg Thieme Verlag Stuttgart, New York, pp. 127–128.

*Primary Examiner*—Michael Buiz
*Assistant Examiner*—David O. Reip
*Attorney, Agent, or Firm*—Ansel M. Schwartz

[57] ABSTRACT

A system for closing together a first side of a sternum and a second side of the sternum of a patient. The system includes a first grommet to be disposed in the first side. The system includes a second grommet adapted to be disposed in the second side. The system includes a mechanism for placing a grommet into the sternum. The placing mechanism is adapted to hold the grommet for placement in the sternum. The system includes a first wire suture for insertion through the first and second grommets. The system includes a stop mechanism for allowing the placing mechanism to place a grommet into the sternum only in a desired location of the patient and any other portion of the patient is protected from damage by the placing mechanism during operation. A grommet. An approximator. A drill stop mechanism. A placement tool. A method of threading a wire suture through a hole in a sternum. A method of bringing together a first side of a sternum and a second side of the sternum.

1 Claim, 15 Drawing Sheets

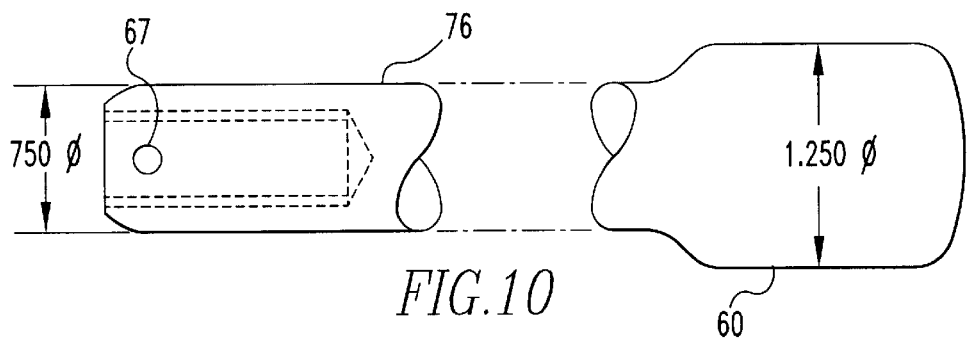
FIG.10
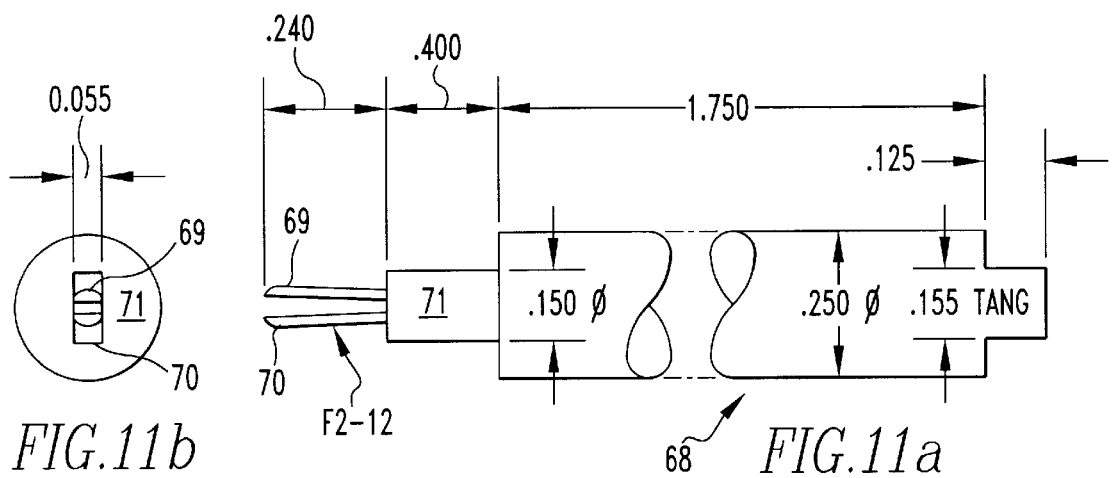
FIG.11b
FIG.11a
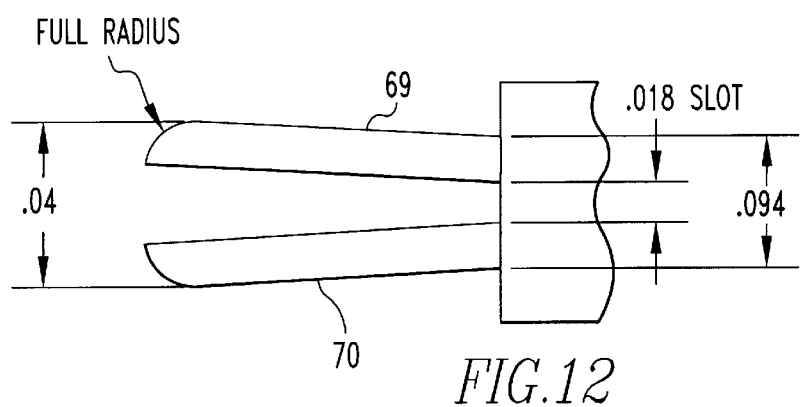
FIG.12

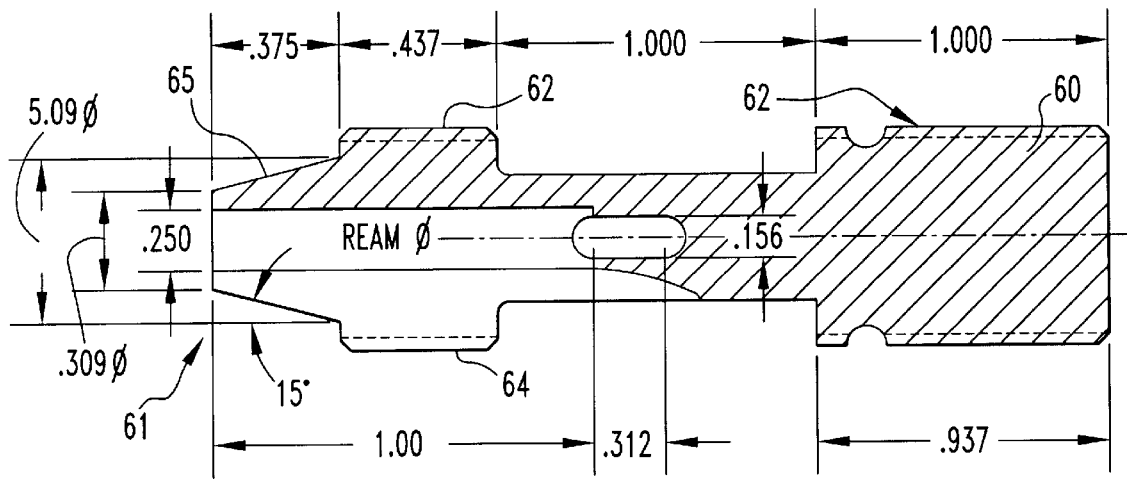
FIG.13
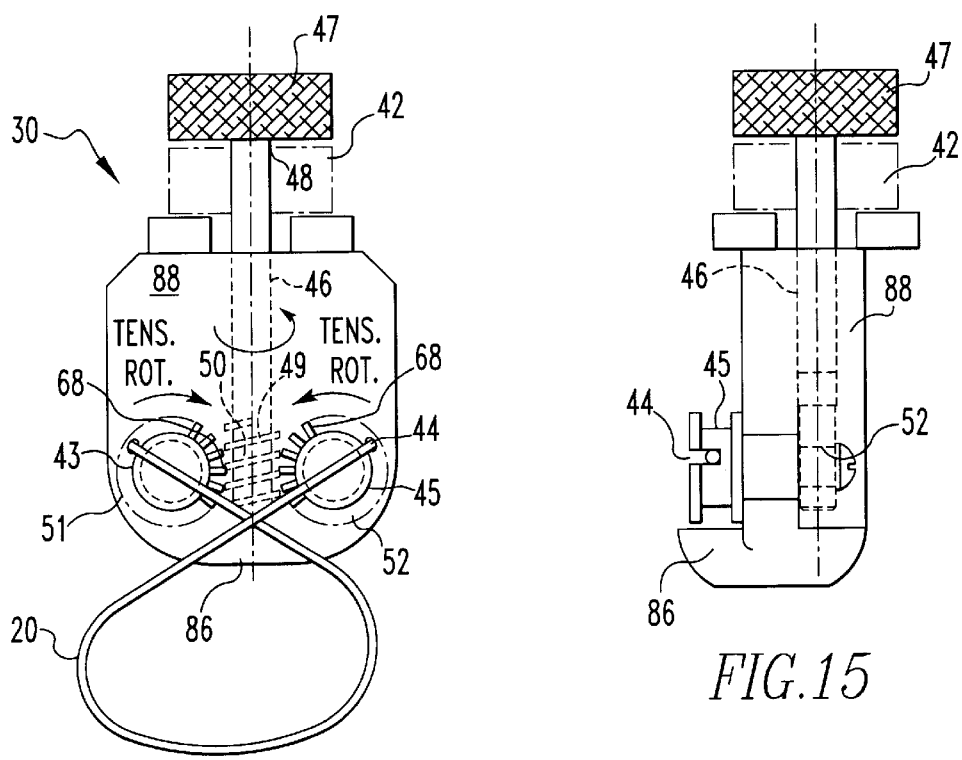
FIG.14
FIG.15

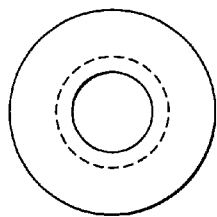 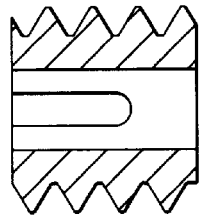 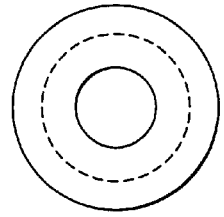
FIG.18c        FIG.18b        FIG.18a
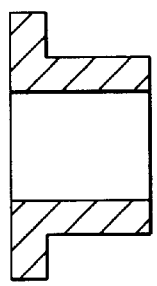 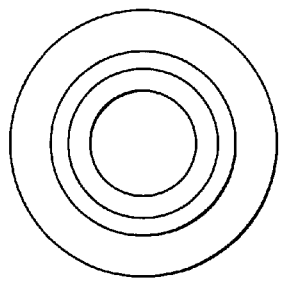
FIG.21b        FIG.21a

UNCRIMPED

CRIMPED
(.25 APPROX.
CRIMPED HEIGHT)

STOP MECHANISM AND METHOD THEREFOR

CROSS-REFERENCE

This application is related to U.S. patent application Ser. No. 09/006,914 filed Jan. 13, 1998 entitled "A SYSTEM, APPARATUS AND METHOD FOR CLOSING SEVERED BONE OR TISSUE OF A PATIENT" by James A. Magovern, incorporated by reference herein.

FIELD OF THE INVENTION

The present invention is related to the closure of hard or soft tissue that has been separated. More specifically, the present invention is related to the closure of a sternum with the use of wire sutures inserted through grommets and placed into the sternum.

BACKGROUND OF THE INVENTION

There are various circumstances in which separated tissue of a patient needs to be brought together so it can heal. Tissue is defined as bone, muscle or fascia that has been divided to gain access the thoracic cavity, mediastinum, or abdomen. For instance, in chest surgery, many times the sternum is separated so a surgeon can again gain access to the chest cavity and organs, muscle and tissue therein. After the surgeon has finished his procedure regarding the chest cavity, the sternum needs to be closed. Key to the healing process of the sternum is the proper stabilization and contact of the two severed sides together. Heretofore, there have been many techniques used to bring the separated sides of the sternum together and maintain them in contact so the healing process can occur. However, these techniques generally limit the movement the patient can experience without damaging or affecting the healing sternum. Furthermore, the process of introducing tools to bring the separated sides of the sternum together can itself create risk or cause damage to the sternum.

The present invention provides for bringing the separate sides of the sternum together while minimizing damage to them and maintaining them while also allowing some flexibility and movement by the patient without disturbing the healing process.

SUMMARY OF THE INVENTION

The present invention pertains to a system for closing together a first side of a sternum and a second side of the sternum of a patient. The system comprises a first grommet to be disposed in the first side. The system comprises a second grommet adapted to be disposed in the second side. The system comprises a mechanism for placing a grommet into the sternum. The placing mechanism is adapted to hold the grommet for placement in the sternum. The system comprises a first wire suture for insertion through the first and second grommets. The system comprises a stop mechanism for allowing the placing mechanism to place a grommet into the sternum only in a desired location of the patient and any other portion of the patient is protected from damage by the placing mechanism during operation.

The present invention pertains to a grommet. The grommet comprises a first portion adapted to engage hard or soft tissue and be seated in the hard or soft tissue. The first portion has a hollow channel extending through it. The grommet comprises a second portion which slides into the first portion through the hollow channel and forms a friction fit with the first portion. The second portion has a hollow channel extending through it.

The present invention pertains to an approximator. The approximator comprises a mechanism for engaging the ends of a wire suture. The approximator comprises a mechanism for tensioning the wire suture. The engaging mechanism is connected to the tensioning mechanism. The approximator comprises a torque limiter in contact with the tensioning mechanism which limits the tension the tensioning mechanism can apply to the wire suture.

The present invention pertains to a drill stop mechanism. The drill stop mechanism comprises a bottom plate adapted to fit underneath hard or soft tissue to stop an object from penetrating past the bottom plate. The drill stop mechanism comprises a mechanism for holding the bottom plate in place about the hard or soft tissue.

The present invention pertains to a grommet placement tool. The grommet placement tool comprises a handle. The grommet placement tool comprises an elongate portion extending from the handle which engages and holds a grommet which is to be inserted into hard or soft tissue.

The present invention pertains to a method of threading a wire suture through a hole in a sternum. The method comprises the steps of inserting a wire passer through the hole so it extends in and through the hole and beneath the sternum. Then there is the step of inserting a wire suture into the wire passer from beneath the sternum.

The present invention pertains to a method of bringing together a first side of a sternum and a second side of the sternum The method comprises the steps of placing a drill stop mechanism under the first side of the sternum. Then there is the step of introducing an object into the first side of the sternum over where the drill stop mechanism is located so the object strikes the drill stop mechanism after it has passed through the first side of the sternum. Next there is the step of removing the object from the first side of the sternum so a hole remains in the sternum. Then there is the step of placing a first grommet in the hole. Next there is the step of placing a second grommet in a hole in the second side of the sternum. Then there is the step of introducing a wire suture into the first and second grommets. Next there is the step of drawing the ends of the wire suture which extend from the first and second grommets together so the first and second sides of the sternum come together. Then there is the step of crimping the ends of the wire suture.

The present invention pertains to a grommet for tissue. The grommet comprises a first portion that is adapted to fix to the bottom of the tissue. The grommet comprises a second portion adapted to fit to the top of the tissue. Preferably, the first portion is threaded and self-tapping and the second portion is adapted to form a friction fit with a hole in the tissue. The second portion has a rim which seats on the top of the surface of the tissue.

The present invention pertains to a method for placing a grommet into a sternum. The method comprises the steps of forming a hole in the sternum. Then there is the step of placing a first portion of the grommet at the bottom of the sternum in the hole. Next there is the step of placing a second portion of the sternum at the top of the sternum in the hole.

The present invention pertains to a method of protecting a patient when forming a hole in the patient. The method comprises the steps of placing a stop mechanism below a portion of the patient where the hole is going to be formed but above the tissue of the patient which is not to have the hole extend into it. Then there is the step of creating the hole.

BRIEF DESCRIPTION OF THE DRAWINGS

In the accompanying drawings, the preferred embodiment of the invention and preferred methods of practicing the invention are illustrated in which:

FIG. 10 is a schematic representation of a side view of a portion of a snap cap placement tool.

FIG. 11a is a schematic representation of a side view of a tool for the snap cap placement tool.

FIG. 11b is a schematic representation of a front view of a tool for the snap cap placement tool.

FIG. 12 is a schematic representation of the first and second tooth of the snap cap placement tool.

FIG. 13 is a schematic representation of a side view of the threaded insert placement tool.

FIG. 14 is a schematic representation of a front view of the approximator.

FIG. 15 is a schematic representation of a side view of the approximator.

FIGS. 18a, 18b and 18c are bottom, side and top views, respectively, of a first portion of an alternative embodiment of a grommet.

FIGS. 21a and 21b are top and side views, respectively, of a second portion of the alternative embodiment of the grommet.

DETAILED DESCRIPTION

Figure 1:
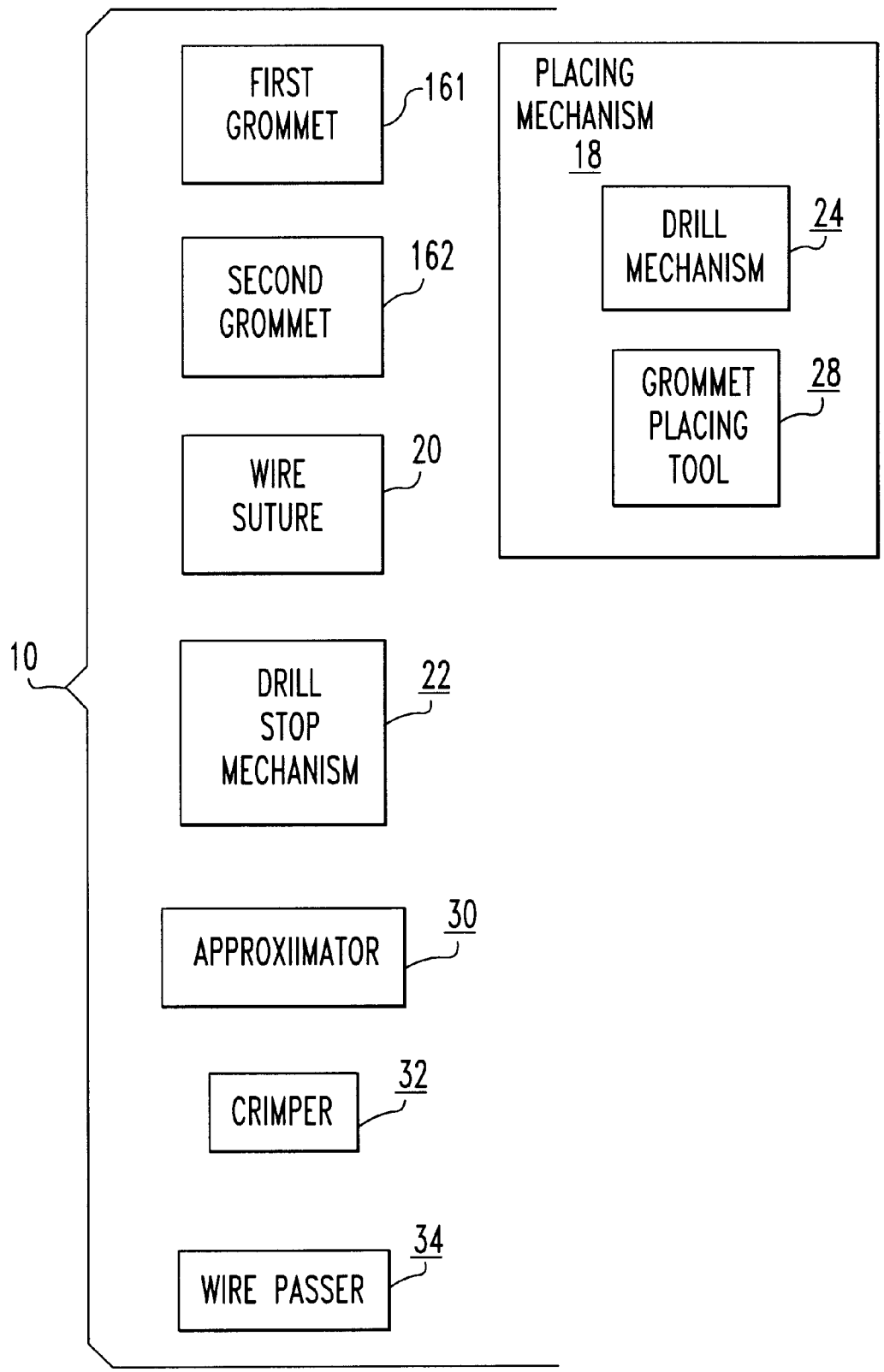
FIG. 1 is a schematic representation of a system of the present invention.
Figure 2:
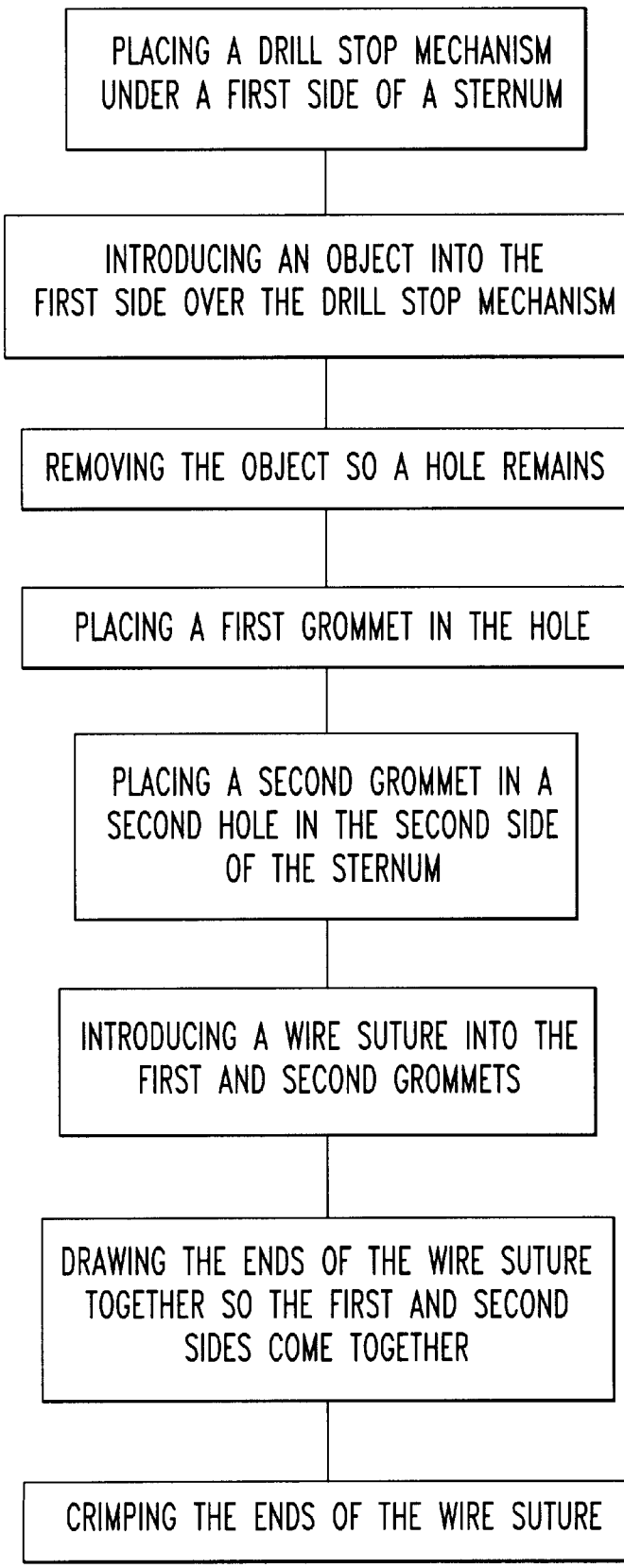
FIG. 2 is a flow chart of a method of the present invention.

Referring now to the drawings wherein like reference numerals refer to similar or identical parts throughout the several views, and more specifically to FIG. 1 thereof, there is shown a system 10 for closing together a first side 12 of a sternum and a second side 14 of the sternum of a patient. The system 10 a first grommet 16l to be disposed in the first side 12. The system 10 comprises a second grommet 16² adapted to be disposed in the second side 14. The system 10 comprises a mechanism 18 for placing a grommet 16 into the sternum. The placing mechanism 18 is adapted to hold the grommet 16 for placement in the sternum. The system 10 comprises a first wire suture 20l for insertion through the first and second grommets 16. The system 10 comprises a drill stop mechanism 22 for allowing the placing mechanism 18 to place a grommet 16 only in a desired location of the patient and any other portion of the patient is protected from damage by the placing mechanism 18 during operation.

Preferably, the placing mechanism 18 includes a drill mechanism 24 for drilling a hole 26 into the sternum in which a grommet 16 is placed. The placing mechanism 18 preferably includes a grommet placement tool 28 which inserts a grommet 16 into the hole 26 drilled by the drill mechanism 24 in the sternum. Each grommet 16 preferably comprises a threaded insert 36 that is adapted to fix to the sternum and a snap cap 38 which fits inside the insert and through which the first wire suture 20l extends.

Preferably, the system 10 includes an approximator 30 adapted for drawing the first and second sides of the sternum together. The system 10 preferably includes a crimper 32 for crimping the first wire suture 20l together when it extends through the first and second grommets 16 in the first and second sides of the sternum. Preferably, the system 10 includes a wire passer 34 which extends through a grommet 16 to facilitate the placement of the first wire suture 20l through the grommet 16.

The present invention pertains to a grommet 16, as shown in FIGS. 6, 7, 8 and 9. The grommet 16 comprises a first portion adapted to engage hard or soft tissue and be seated in the hard tissue, such as bone or cartilage, for instance of a sternum, or soft tissue. The first portion has a hollow channel 33 extending through it. The grommet 16 comprises a second portion which slides into the first portion through the hollow channel 33 and forms a friction fit with the first portion. The second portion has a hollow channel 37 extending through it. Preferably, the first portion is a threaded insert 36 which is self-tapping, and the second portion is a snap cap 38 having a bulge 39 in its outside surface 40.

Figure 16:
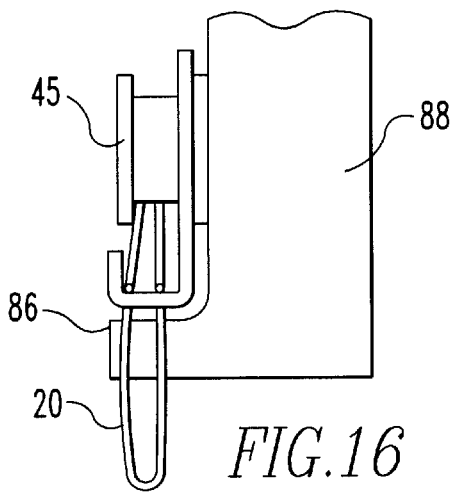
FIG. 16 is a schematic representation of a side view of the spool and anvil of the approximator.

The present invention pertains to an approximator 30, as shown in FIGS. 14, 15 and 16. The approximator 30 comprises a mechanism for engaging the ends of a wire suture 20. The approximator 30 comprises a mechanism for tensioning the wire suture 20. The engaging mechanism is connected to the tensioning mechanism. The approximator 30 comprises a torque limiter 42 in contact with the tensioning mechanism which limits the tension the tensioning mechanism can apply to the wire suture 20.

Preferably, the engaging mechanism includes a first spool 43 having a slot 44 and a second spool 45 having a slot 44. Each slot 44 is engaged to hold an end of the wire suture 20. The tensioning mechanism preferably includes an axle 46 having a tensioning knob 47 at its top 48 and a worm 49 at its bottom 50. The torque limiter 42 is disposed about the axle 46 and between the knob 47 and the worm 49. There is a first worm gear 51 and a second worm gear 52. Each worm gear is engaged with the worm 49. The first spool 43 extends from the first worm gear 51 and the second spool 45 extends from the second worm gear 52.

Figure 4:
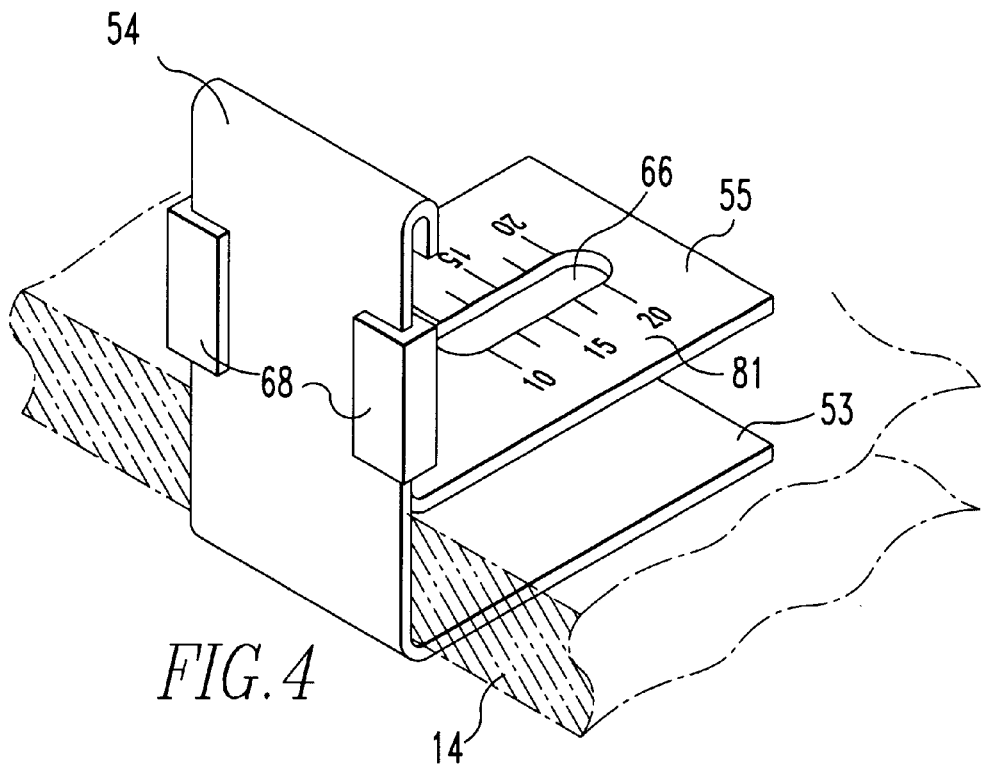
FIG. 4 is a schematic representation of a perspective view of a drill stop mechanism.
Figure 5:
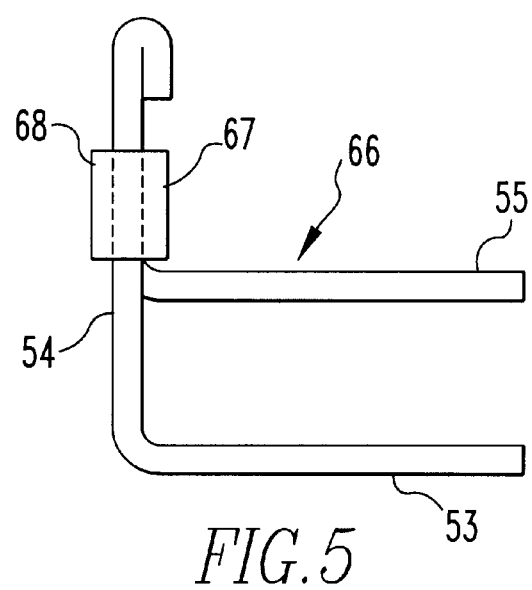
FIG. 5 is a schematic representation of a side view of the drill stop mechanism.

The present invention pertains to a drill stop mechanism 22, as shown in FIGS. 4 and 5. The drill stop mechanism 22 comprises a bottom plate 53 adapted to fit underneath hard or soft tissue to stop an object from penetrating past the bottom plate 53. The drill stop mechanism 22 comprises a mechanism for holding the bottom plate 53 in place about the hard or soft tissue. Preferably, the holding mechanism includes a side plate 54 which forms an angular relationship with the bottom plate 53 and is attached to the bottom plate 53, and a top plate 55 which is slidably connected to the side plate 54 and is adapted to fit over the hard or soft tissue under which the bottom plate 53 is disposed.

The present invention pertains to a grommet placement tool 28, as shown in FIGS. 10, 11a, 11b, 12 and 13. The grommet placement tool 28 comprises a handle 60. The grommet placement tool 28 comprises an elongate portion extending from the handle 60 which engages and holds a grommet 16 which is to be inserted into hard or soft tissue.

The elongate portion can include a collet stem 61 having a first plate 62 and a second plate 64 which fits into a threaded insert 36 and an end 65 which extends forward from the first and second plates which fits into the threaded insert 36 to hold the threaded insert 36. The handle 60 can have a pin assembly 76 with a pin hole 26 and the elongate portion can include a holding tool 68 that attaches to the pin assembly 76 through the pin hole 26. The holding tool 68 has a first tooth 69 and an opposing second tooth 70 which angle away from each other and extend from the head 71 of the tool 68. The first tooth 69 and second tooth 70 are adapted to be inserted into a snap cap 38 of a grommet 16 to hold the snap cap 38 by spring pressure in place.

Figure 17:
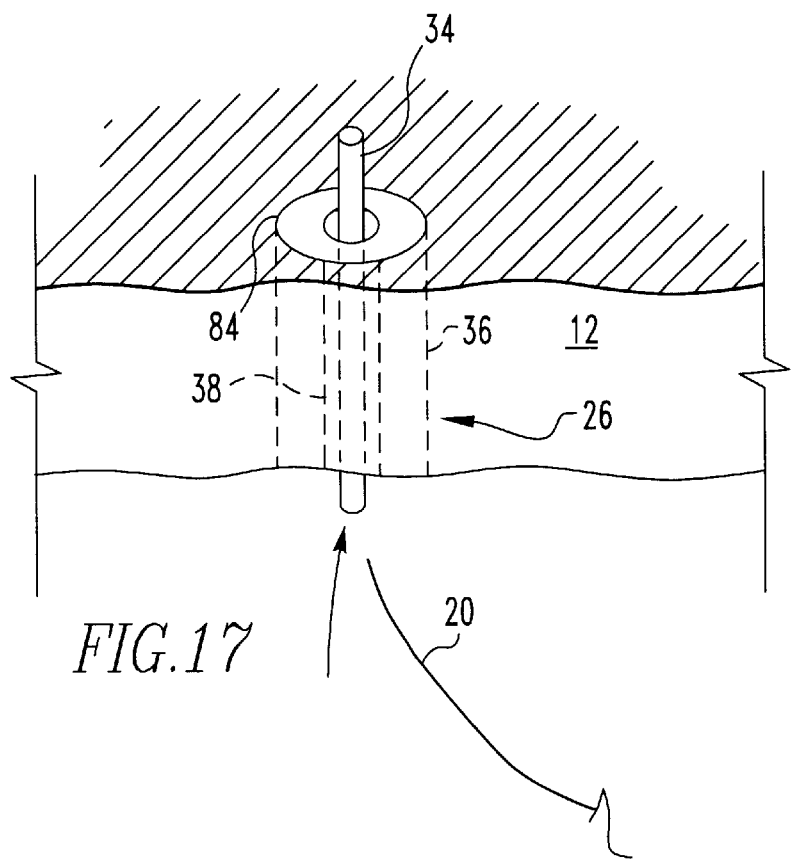
FIG. 17 is a schematic representation of a perspective view of a wire passer extending through the sternum.

The present invention pertains to a method of threading a wire suture 20 through a hole 26 in a sternum, as shown in FIG. 17. The method comprises the steps of inserting a wire passer 34 through the hole 26 so it extends in and through the hole 26 and beneath the sternum. Then there is the step of inserting a wire suture 20 into the wire passer 34 from beneath the sternum.

The present invention pertains to a method of bringing together a first side 12 of a sternum and a second side 14 of the sternum. The method comprises the steps of placing a drill stop mechanism 22 under the first side 12 of the sternum. Then there is the step of introducing an object, such as a drill, into the first side of the sternum over where the drill stop mechanism 22 is located so the object, such as a drill, strikes the drill stop mechanism 22 after it has passed through the first side 12 of the sternum. Next there is the step of removing the object from the first side 22 of the sternum so a hole 26 remains in the sternum. Then there is the step of placing a first grommet 161 in the hole 26. Next there is the step of placing a second grommet 162 in a hole 26 in the second side 14 of the sternum. Then there is the step of introducing a wire suture 20 into the first and second grommets. Next there is the step of drawing the ends of the wire suture 20 which extend from the first and second grommets together so the first and second sides of the sternum come together. Then there is the step of crimping the ends of the wire suture 20.

The present invention pertains to a grommet for tissue. The grommet comprises a first portion that is adapted to fix to the bottom of the tissue. The grommet comprises a second portion adapted to fit to the top of the tissue. Preferably, the first portion is threaded and self-tapping and the second portion is adapted to form a friction fit with a hole in the tissue. The second portion has a rim which seats on the top of the surface of the tissue.

The present invention pertains to a method for placing a grommet into a sternum. The method comprises the steps of forming a hole in the sternum. Then there is the step of placing a first portion of the grommet at the bottom of the sternum in the hole. Next there is the step of placing a second portion of the sternum at the top of the sternum in the hole.

The present invention pertains to a method of protecting a patient when forming a hole in the patient. The method comprises the steps of placing a stop mechanism below a portion of the patient where the hole is going to be formed but above the tissue of the patient which is not to have the hole extend into it. Then there is the step of creating the hole.

Figure 3:
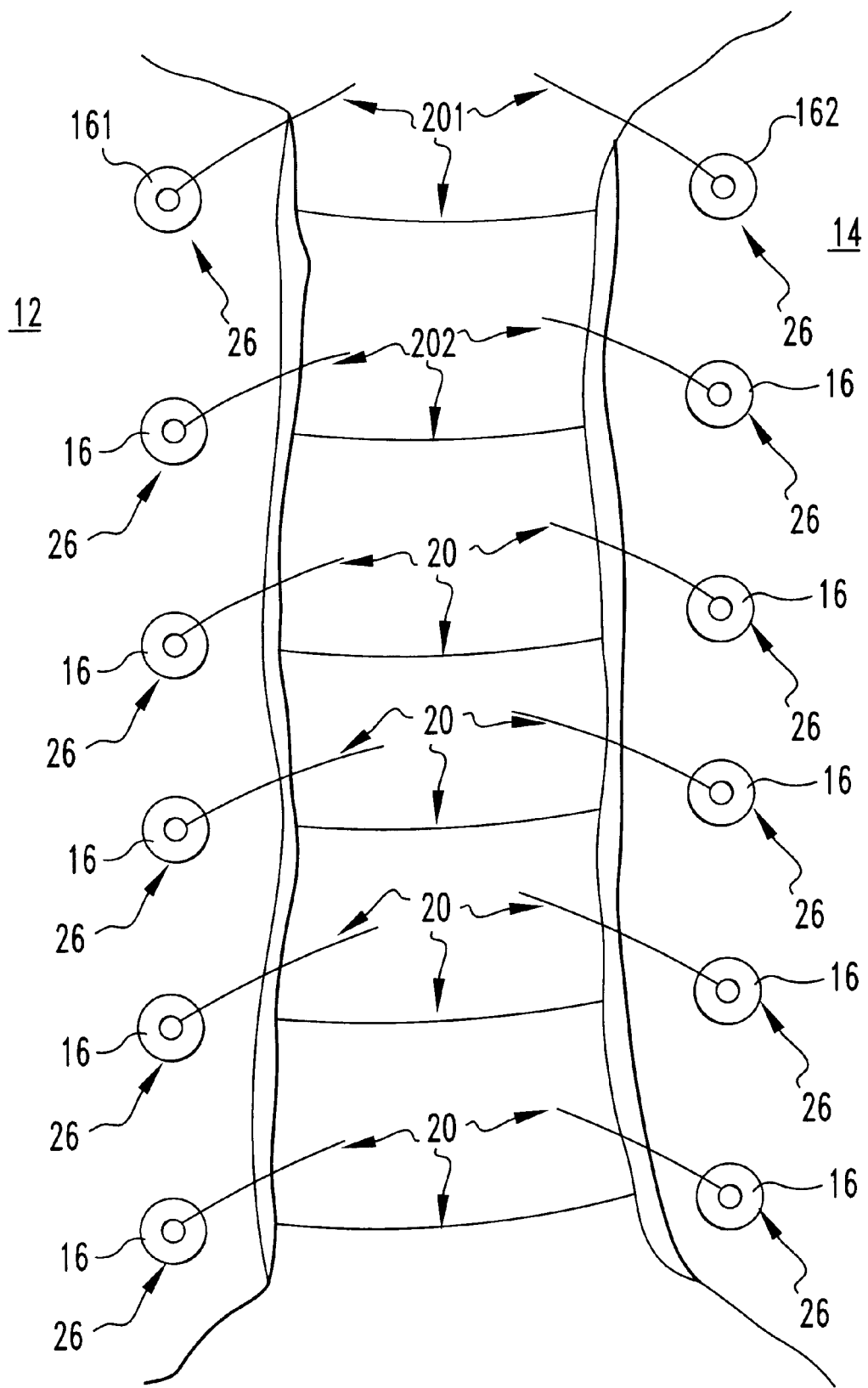
FIG. 3 is a perspective view of a sternum with grommets.

In the operation of the invention, when the surgeon is ready to bring the first side 12 and second side 14 of the sternum together to close the sternum, as shown in FIG. 3, the surgeon or a designated individual or individuals take a drill hand unit and prepare to drill holes 26 into the first side 12 and second side 14 of the sternum. The drill hand unit is connected to a drill power supply, such as a battery powered drill, to operate the drill hand unit. The drill hand unit is of standard issue well known to one skilled in the art. The drill hand unit has inserted into it a drill bit having a diameter of between 3.6–4.0 millimeters and preferably about 0.15 inches (3.8 millimeters). The drill bit is of standard issue well down to one skilled in the art.

In preparation for drilling the first hole 26 through the first side 12 of the sternum, a drill stop mechanism 22 is positioned about the sternotomy cut edge of the first side 12, as shown in FIGS. 4 and 5. The drill stop mechanism 22 is comprised of a top plate 55 and an opposing bottom plate 53 to the top plate 55. The bottom plate 53 extends from a side plate 54 as one piece and the side plate 54 forms essentially a right angle with the bottom plate 53. The bottom plate 53 is solid with no openings or slots or holes. The bottom plate 53 is what the drill bit strikes after it has drilled through the first side 12 of the sternum and prevents the drill bit from drilling or striking any other part of the patient. Extending from the top plate 55 at essentially a right angle in one continuous piece is a top plate edge 67 with ears 68. The ears 68 are folded about the side plate 54 to cause the top plate 55 to become captive with the side plate 54. The top of the side plate 54 is folded down to capture the top plate 55 so it cannot be lifted up and off of the side plate 54. The ears 68 prevent the top plate 55 from being moved sideways and removed from the side plate 54.

The top plate 55 has a top plate slot 66 which forms a target for the drill bit to assure that the drill bit will always hit the bottom plate 53, without having to make the bottom plate 53 any larger than necessary. The top plate 55 moves up and down along the side plate 54 through the ears 68 so the space between the top plate 55 and bottom plate 53 can be adjusted. When the drill stop mechanism 22 is placed about the first side 12 of the sternum, the top plate 55 is slid up along the side plate 54 to provide a greater thickness then the thickness of the first side 12 of the sternum so the bottom plate 53 can be slid under the first side 12 of the sternum and the top plate 55 can be slid over the top of the sternum until the sternotomy cut edge of the first side 12 of the sternum contacts the side plate 54 which stops the drill stop mechanism 22 from further movement over the first side 12 of the sternum. The top plate 55 is then released and falls onto the top side of the first side 12 of the sternum, aligning a target for the drill bit through the slot 66 of the top plate 55. The slot 66 of the top plate 55 has gradations 81 along it to better identify the drill spot position for the drill bit to properly drill the hole 26 in the desired position in the first side 12 of the sternum.

The process described for drilling the first hole 26 in the first side 12 of the sternum is repeated for as many holes 26 as are deemed appropriate in the first side 12 of the sternum and the second side 14 of the sternum. Typically, ten holes 26 are drilled in the sternum, five in the first side 12 and five in the second side 14 (more for larger/taller people) of the sternum, with each hole 26 in the first side 12 of the sternum having an opposing hole 26 drilled in the second side 14 of the sternum and in alignment with the corresponding hole 26 in the first side 12 of the sternum. Typically, several inches will separate each hole 26 in the respective sternum so enough of the sternum separates the holes 26 to provide strong structural integrity between the holes 26 and there will be no cracks or stress fractures between the drill holes 26. The holes 26 are drilled approximately 1 cm from the incision and are of a standard size to fit the threaded inserts 36 of the grommets 16.

Figure 6:
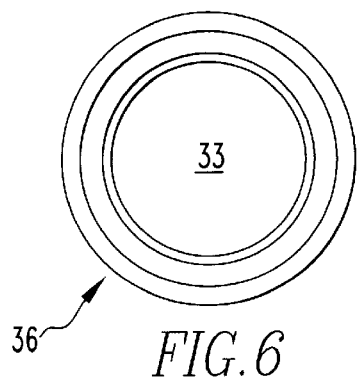
FIG. 6 is a schematic representation of a bottom view of a threaded insert.
Figure 8:
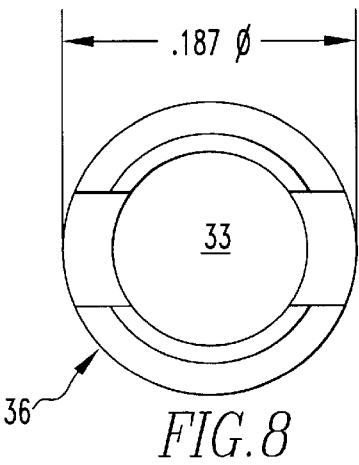
FIG. 8 is a schematic representation of a top view of a threaded insert.
Figure 7:
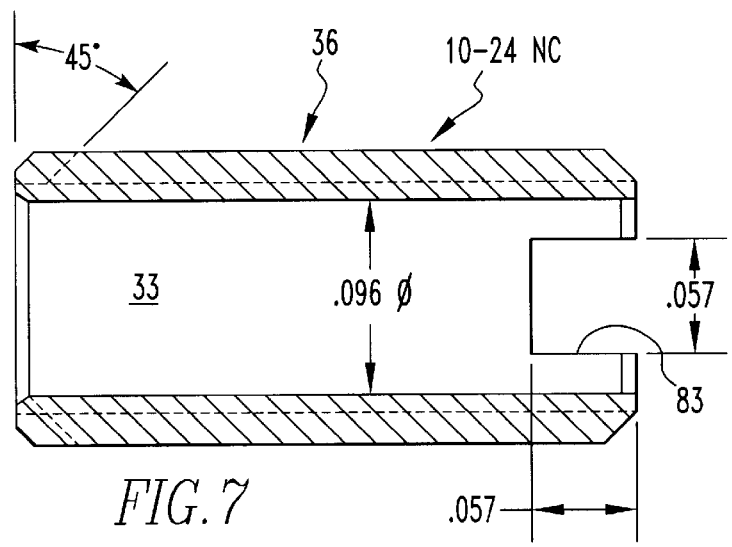
FIG. 7 is a schematic representation of a side in view of a threaded insert.
Figure 9:
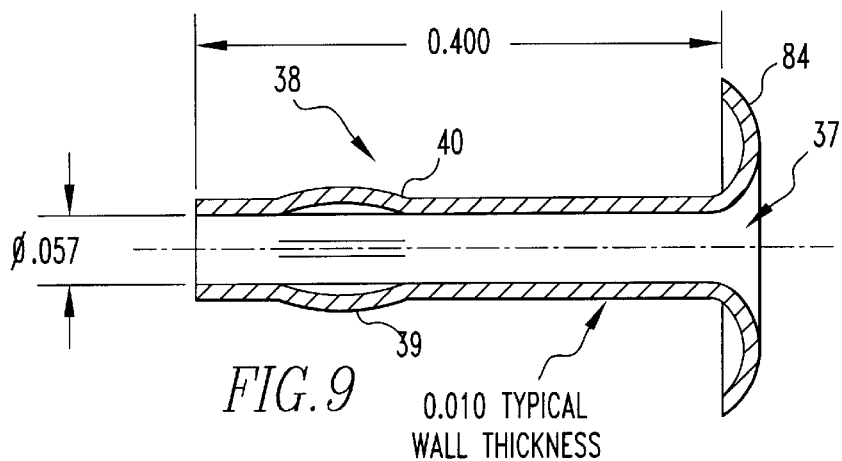
FIG. 9 is a schematic representation of a side view of a snap cap.

After the holes 26 are drilled into the first and second sides of the sternum, the grommets 16 comprised of threaded inserts 36 as shown in FIGS. 6, 7 and 8, and snap caps 38, as shown in FIG. 9, are introduced into the holes 26 in the first and second sides of the sternum. The threaded inserts 36 and snap caps 38 of the grommets 16 are introduced into the first and second sides of the sternum with two separate grommet placement tools that are in use at the same time during the operation. One grommet placement tool 28, the snap cap placement tool 29, is to hold the snap caps 38 and a second grommet placement tool 28, the threaded insert placement tool 27, is to hold the threaded inserts 36. During the operation, the surgeon's assistant loads a snap cap 38 on the snap cap placement tool 29, as shown in FIGS. 10, 11a, 11b and 12, while the surgeon is screwing the threaded insert 36 with the threaded insert placement tool 27 into a hole 26 in the first side 12 of the sternum. When the surgeon is finished screwing the threaded insert 36 into the hole 26 in the first side 12 of the sternum, the surgeon switches the now empty insert placement tool 27, as shown in FIG. 13, with a loaded snap cap placement tool 29 that is being held by the assistant. The surgeon then places the snap cap 38 into the threaded insert 36 that the surgeon just screwed into the hole 26 in the first side 12 of the sternum.

After the surgeon has switched the insert placement tool 27 with the snap cap placement tool 29 and while the surgeon is placing the snap cap 38 into the threaded insert 36, the assistant loads the threaded insert 36 into the insert placement tool 27 just handed to the assistant. By doing this, when the surgeon finishes placing the snap cap 38 into the threaded insert 36, the insert placement tool 27 is loaded and ready for the surgeon to switch the now empty snap cap placement tool 29 with the loaded insert placement tool 27 to screw the next threaded insert 36 into the next hole 26 in the first side 12 or second side 14 of the sternum, as the surgeon sees fit. The assistant then loads the snap cap placement tool 29 so the procedure is ready to occur again. This process is repeated until all of the grommets 16 are in place in all of the holes 26.

The threaded insert 36 is of a hollow cylindrical shaped bone screw which on its leading end is self tapping. The diameter of the threaded insert 36 is 0.187 inches and the hole 26 drilled into the sternum is of a slightly smaller diameter. The trailing end of the threaded insert 36 has a screw driver slot 83 to receive the threaded insert placement tool 27 so the threaded insert placement tool 27 can hold the threaded insert 36 and screw the threaded insert 36 into the hole 26 in the sternum. Both the leading end and trailing end are chamfered so there are no sharp edges to tear or crack the sternum or cartilage in the sternum. The threaded insert 36 is made of 316 L stainless steel. The threaded insert 36 is provided in two lengths, 0.3 inches and 0.5 inches.

The snap cap 38 slides into the threaded insert 36 once the insert is screwed into the bone. It is held in place by a friction fit. The snap cap 38 is hollow whose trailing end has a flange 84 which seats on the trailing edge of the threaded insert 36 and the top of the sternum. In approximately the center of the snap cap 38 is a bulge 39 in its cylindrically shaped outer surface 40. The bulge 39 provides a spring-like effect to hold the snap cap 38 in the threaded insert 36 by a friction fit. The bulge 39 is achieved in the snap cap 38 by compressing the snap cap 38 in its axial direction by known techniques.

The threaded insert placement tool 27 has a screw driver handle 60 with a collet stem 61 that is made of stainless steel. The collet stem 61 has a first plate 62 and a second plate 64 which acts as a screw driver head and fits into the screw driver slot 83 of the threaded insert 36. Extending forward from the blades is an end 65 that angles inwards to fit into the hollow center of the threaded insert 36 to further assist in holding the threaded insert 36 to the collet stem 61. The center of the collet stem 61 is hollow. When the handle 60 is turned, the first and second blades of the collet stem 61 are also turned, which results in the threaded insert 36 being turned and consequently screwed into the bone or cartilage around the hole 26 as the threaded insert placement tool 27 is rotated.

The snap cap placement tool 29 is comprised of a handle 60 with a pin assembly 76 and a holding tool 68 that attaches to the pin assembly 76 through the pin hole 67. The tool 68 has a first tooth 69 and an opposing second tooth 70 which angle away from each other and extend from the head of the tool. The first tooth 69 and second tooth 70 are squeezed together upon insertion into the hollow center of the snap cap 38. By the first tooth 69 and second tooth 70 being squeezed together, a spring pressure from the first tooth 69 and second tooth 70 trying to expand back to their equilibrium position is created against the inside surface of the snap cap 38. This spring pressure serves to hold the snap cap 38 on the first tooth 69 and second tooth 70 of the snap cap placement tool 29 and if necessary the head 71 pushes against the snap cap 38 during placement to push the snap cap 38 into the threaded insert 36. The spring pressure is less than the friction fit force created by the bulge 39 of the snap cap 38 against the interior of the threaded insert 36 once the snap cap 38 is inserted into the threaded insert 36. When the snap cap placement tool 29 is withdrawn after the snap cap 38 has been inserted into the threaded insert 36, and there is nothing to drive against the snap cap 38, such as the head 71 when the snap cap 38 is being inserted into the threaded insert 36, the snap cap 38 is held in place in the threaded insert 36 and the snap cap placement tool 29 separates from the snap cap 38.

Figure 19:
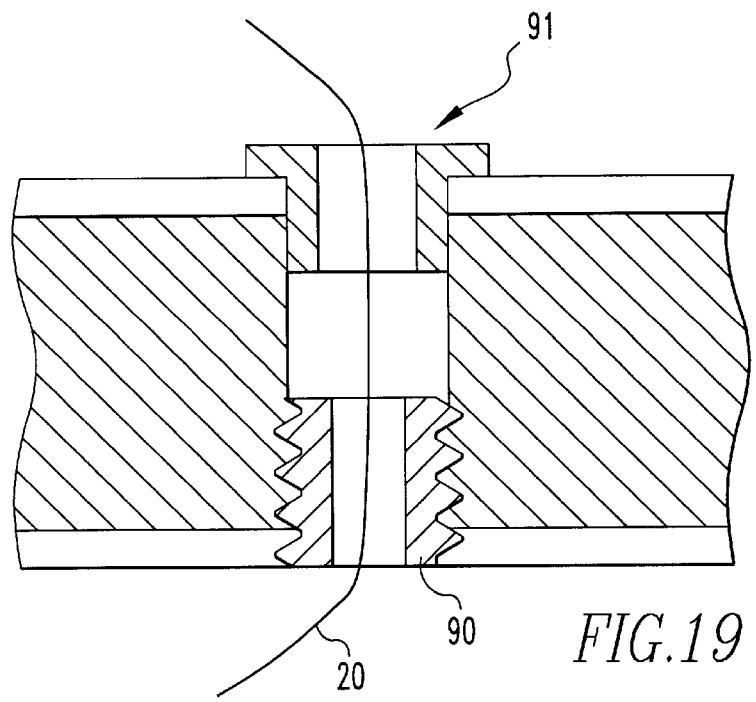
FIG. 19 is a schematic representation of the alternative embodiment of a grommet in hard tissue.
Figure 20:
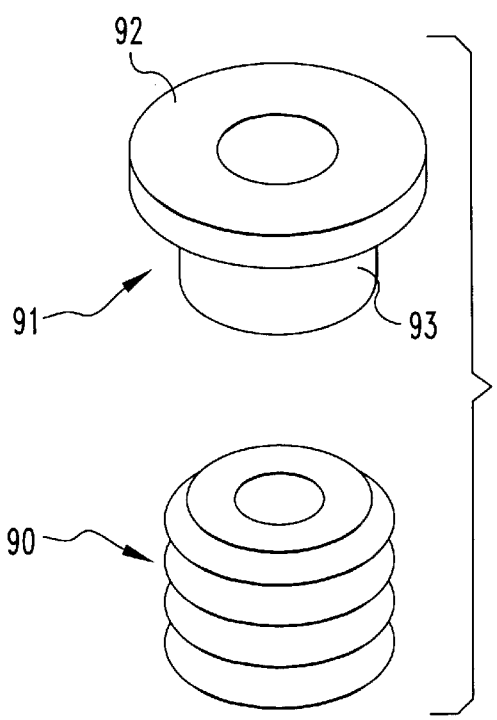
FIG. 20 is a schematic representation of the alternative embodiment of the grommet.

In an alternative preferred embodiment of the grommet and referring to FIGS. 19 and 20, the grommet is comprised of a first portion 90 which is threaded and self-tapping and a second portion 91 which is adapted to form a friction fit with a hole in the sternum. The second portion 91 has a rim 92 which seats on the top of the surface of the sternum. The second portion 91 has a tube 93 extending down into the hole which forms the friction fit from the rim 92. The first and second portions are made of stainless steel. Alternatively, the second portion can also be threaded.

Placement occurs similarly to the embodiment of the grommet described above. With this embodiment of the grommet, the grommet placement tool 28 also includes a threaded insert placement tool 27 which holds the first portion 90 of the grommet. With the first portion 90 loaded on the threaded insert placement tool 27, the surgeon screws the first portion 90 into the hole and down to the bottom of the hole 26. The surgeon can tell when the first portion 90 has reached the bottom of the hole 26 in the sternum by simply placing his finger on the hole 26 under the sternum and feeling the first portion 90 contact his finger as it reaches the bottom of the sternum. The surgeon then lifts the threaded insert placement tool 27 out of the hole 26, with the first portion 90 remaining threaded into the sternum in the hole 26.

The surgeon then hands the empty threaded insert placement tool 27 to the surgeon's assistant and takes a second portion 91 placement tool 29, which is essentially the same as the snap cap placement tool 29, that is loaded with the second portion 91. The surgeon inserts the tube 93 of the second portion 91 into the hole 26 and firmly and carefully applies force downward with the second portion 91 placement tool 29 on the second portion 91, causing the second portion 91 to penetrate into the hole 26 and form a friction fit with the hole 26. The second portion 91 will continue to penetrate into the hole until the rim 92 seats onto the sternum surface, causing the second portion 91 to stop moving into the hole.

The first portion 90 protects the bottom of the sternum from the wire suture rubbing or tearing the sternum when tension is placed on the wire suture 20. Similarly, the second portion 91 protects the top of the sternum from the wire suture rubbing or tearing the sternum when tension is placed on the wire suture. The two critical locations on the sternum in regard to the wire suture are the top of the sternum where the wire suture 20 bends and the bottom of the sternum with the wire suture 20 bends and can put localized force on the sternum at the bending point where the force from the wire suture 20 is essentially against the sternum. The wire suture 20 extending along the hole in the sternum does not put significant force on the sternum or cartilage within the sternum since it does not bend and pull against the sternum when the wire suture is tensioned.

Once the grommets 16 are in place, the wire sutures 20 are placed through the grommets 16-one wire suture 20 for each pair of grommets 16 that are in alignment across from each other. The wire suture 20 is a standard stainless steel wire used for sternal closure. It is 316 L stainless steel suture USP size 5. The end of the wire suture 20 is pushed down through the grommet 16 on the first side 12 of the sternum and a wire passer 34 is pushed down through the corresponding grommet 16 on the second side 14 of the sternum. The wire passer 34 is a small hollow flexible tube that is inserted through the grommet 16 to assist the surgeon in locating the hole 26 from the underside of the sternum. The end of the wire suture 20 that has passed through the grommet 16 in the first side 12 of the sternum is now within the chest. The wire suture 20 is then bent and brought across to the wire passer 34 where it is inserted into the end of the wire passer 34 that extends into the chest through the grommet 16 in the second side 14 of the sternum, as shown in FIG. 17. When passing the wire suture 20 from within the sternum through the grommet 16, the surgeon will simply insert the end of the wire into the wire passer 34 and feed it through to the top side of the patient's sternum. Once the wire suture 20 is through, the wire passer 34 is pulled up through the grommet 16 and along the wire suture 20 until it is removed from the wire suture 20. Once the wire passer 34 is removed, the wire suture 20 is left in place extending through both grommets 16. This process is repeated until wire sutures 20 have been placed through each pair of grommets 16 in the sternum.

Each wire suture 20, beginning at the top of the sternum, is then tensioned (pulling the edges of the sternotomy together) using the sternal approximator 30, as shown in FIGS. 14, 15 and 16, and crimped. The sternal approximator 30 is used to tension the wire sutures 20 used for sternal closure. The sternal approximator 30 applies nearly equal force to each end of the wire suture 20 for purposes of improved stability of the closure.

The approximator 30 has a first spool 43 and an opposing second spool 45. The end of the wire suture 20 extending from the grommet 16 in the first side 12 of the sternum is placed in the slot 44 in the second spool 45. The slot 44 holds the end of the wire suture 20 in the spool. Similarly, the end of the wire suture 20 extending from the grommet 16 in the second side 14 of the sternum is placed in the slot 44 and the first spool 43. In this way, the ends of the wire suture 20 cross over each other and extend across an anvil 86 at the base of the approximator 30. The anvil 86 is present to crimp the wire suture ends against to more efficiently apply tension to the wire suture 20. The first spool 43 extends from the first worm gear 51 of the approximator 30 and the second spool 45 extends from the second worm gear 52 of the approximator 30. Each worm 49 gear engages a worm 49 that is disposed at the bottom of an axle 46 which extends through the center of the approximator 30.

At the top of the axle 46 is a tensioning knob 47 which is used to rotate the axle 46 and thus the wire. Rotation of the worm 49 causes the worm gears 68 to rotate toward each other and tension the wire suture 20 as each end of the wire suture 20 wraps around the respective spool as they rotate. To ensure that the wire suture 20 is not tensioned more then necessary and cause damage to the sternum, for instance by crushing each side of the sternum together, a torque limiter 42 is disposed between the tensioning knob 47 and the frame 88 of the approximator 30. The tensioning knob 47 cannot rotate past the torque limiter 42, hence controlling the extent the knob can be tensioned. The free ends of the wire suture 20 are then crimped together, for instance with a pliers which grips the ends and is than rotated. Any additional unnecessary length of wire suture 20 is then cut and the crimped ends of the wire suture 20 are then folded down upon the sternum. Closure of the superficial incision then proceeds normally.

When the tensioning is complete and the action of the approximator 30 on the wire suture 20 has caused each end of the wire suture 20 to be pulled together and thus each end of the sternum through which each end of the wire suture 20 extends, the tensioning knob 47 is rotated in the opposite direction to unwind the ends of the wire suture 20 from the spool. When the ends of the wire suture 20 are completely unraveled from the spools, each end of the wire suture 20 is removed from the slot 44 it is in of the spool. The tension on the wire suture 20 that is through the grommets 16 and within the chest relaxes somewhat but the sides of the sternum remain in place since there is little force present to separate each side of the sternum. The presence of the grommets 16 serves to protect the sternum from the wire suture 20 tearing or rubbing against it during the tensioning process and during the healing process where movement of the patient can create forces on each side of the sternum which would cause the sternum to separate were it not for the wire sutures 20 in place.

The presence of individual grommets as anchoring points through which the wire sutures extend, serves to allow the patient flexibility to move while minimizing the risk of tearing the healing incision. Each grommet is independent of any other grommet so no forces are created between the grommets that would contribute to injuring the patient when the patient moves. Only the individual wire sutures connect two grommets, but the wire suture inherently allows for some movement while still providing structural support to maintain the two sides of the sternum together.

Figure 22:
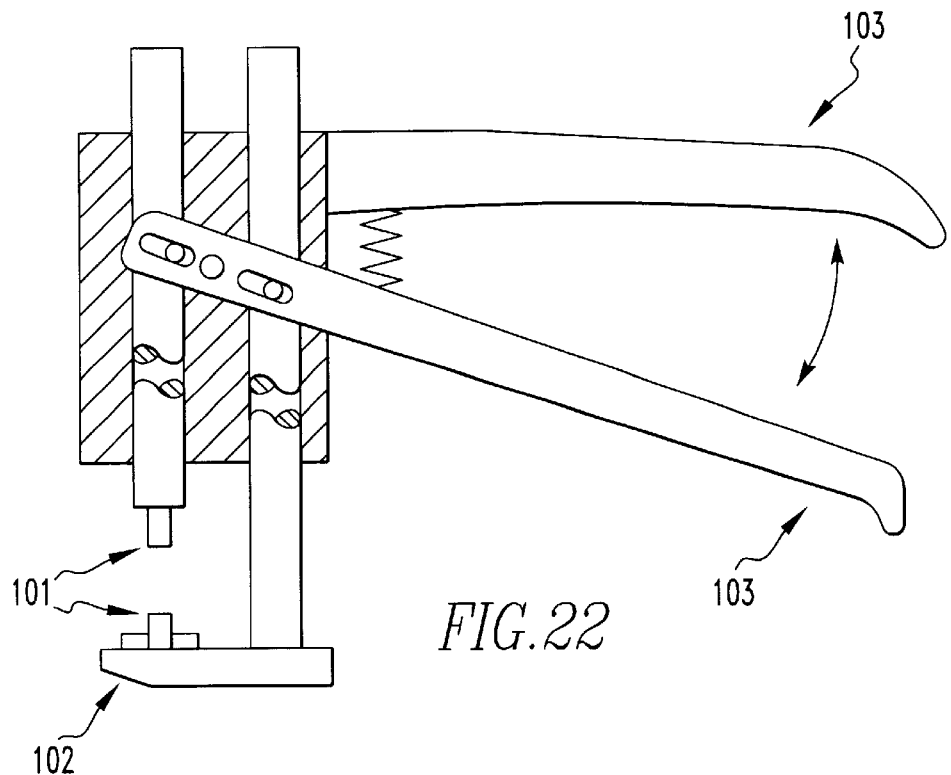
FIG. 22 is a schematic representation of an alternative embodiment of a grommet placing mechanism.

Referring to FIG. 22, there is shown an alternative of the placing mechanism. The grommet is placed on the tips 101 of the placing mechanism. The base 102 of the placing mechanism is inserted under the sternum and then the grips 103 are squeezed together to introduce the grommet into the sternum.

Figure 23:
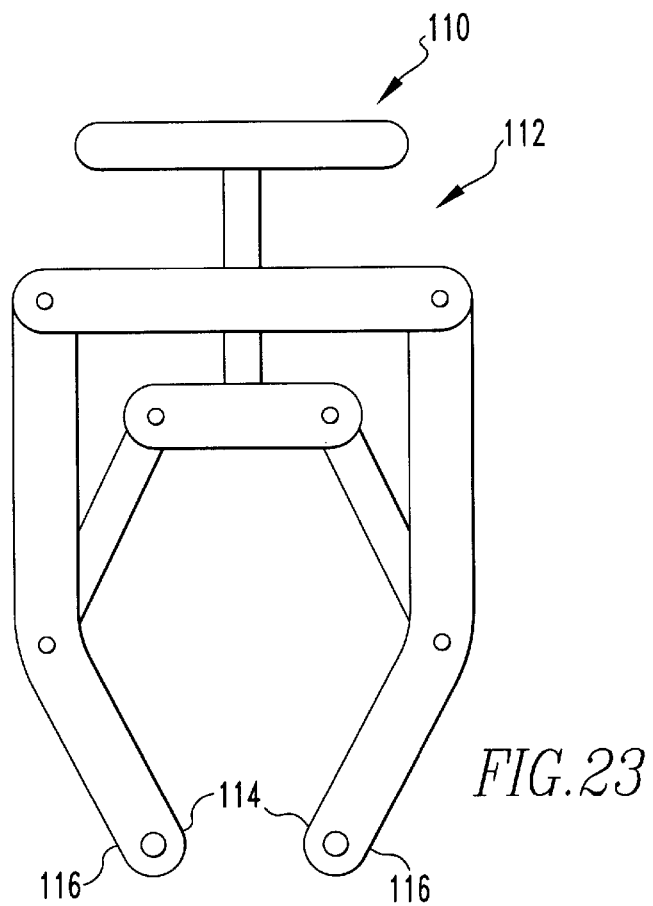
FIG. 23 is a schematic representation of the alternative embodiment of an approximator.

FIG. 23 shows an alternative embodiment of an approximator. In this embodiment, there is a torque gauge 110 that is disposed on a threaded shaft 112. When the torque gauge 110 is rotated, clamps 114 are closed together, pulling wires that have been inserted through holes 116 in the clamps. The torque gauge 110 reveals the level of tension on the wire suture 20 being pulled together.

Figure 24:
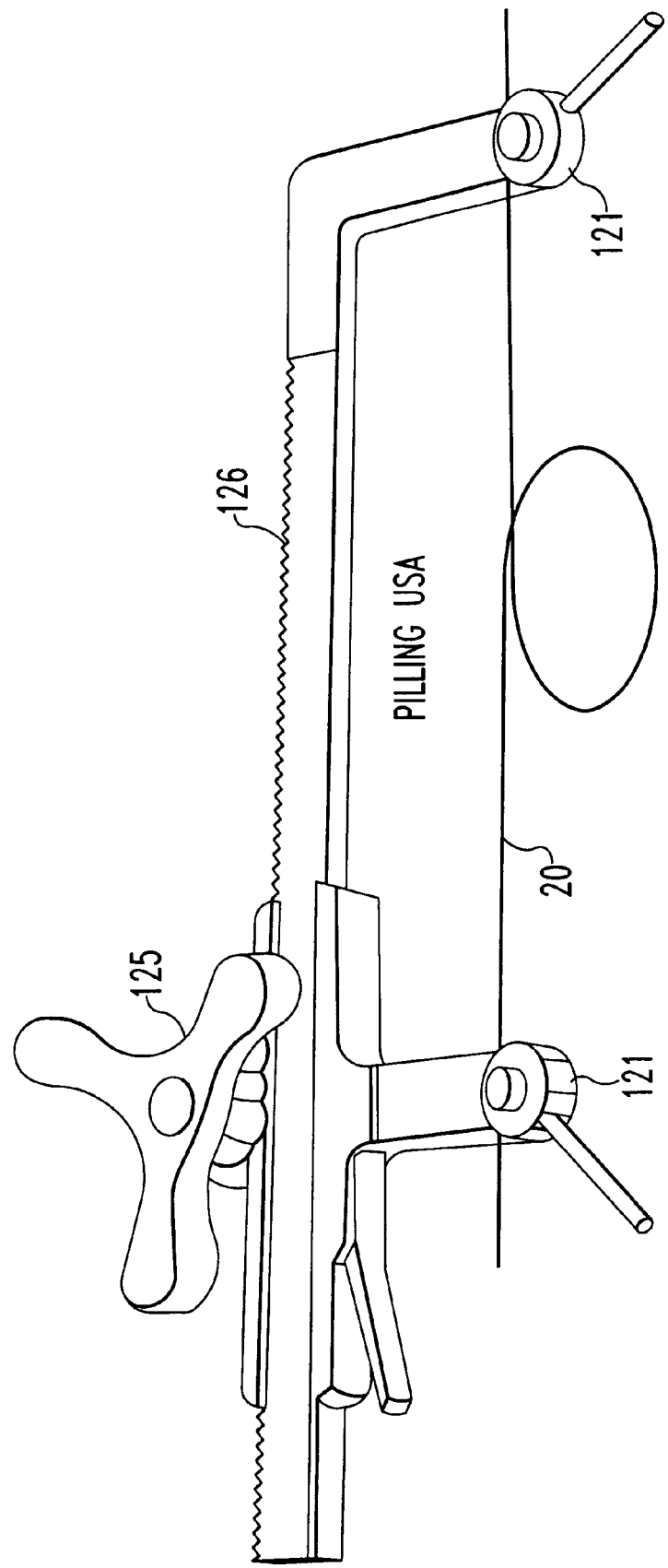
FIG. 24 is a schematic representation of an alternative embodiment of an approximator.

FIG. 24 shows another alternative embodiment of an approximator. The wire suture 20 is connected to two respective clamps 121. A handle 125 is rotated on a rack and opinion gear 126 causing the wire suture 20 to be tensioned.

Figure 25:
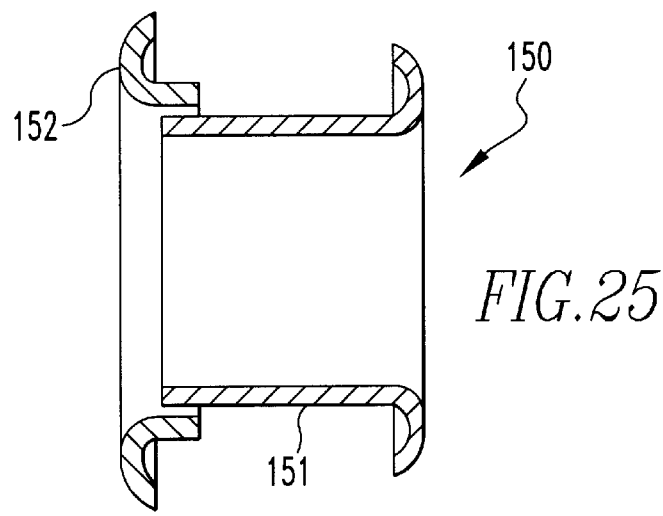
FIGS. 25, 26 and 27 are schematic representations of a biodegradable grommet.
Figure 26:
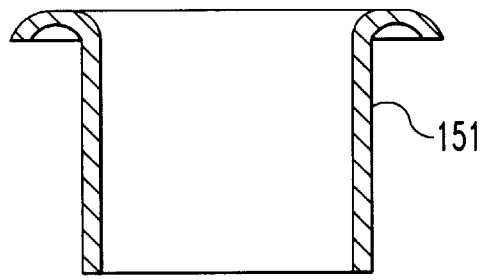
Figure 27:
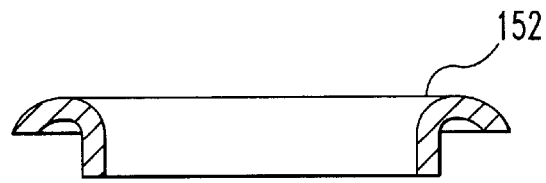

FIG. 25 shows an assembled biodegradable grommet 150. The biodegradable grommet can be made from polyglycolide. The grommet 150 is comprised of a male piece 151 shown in FIG. 26 and a female piece 152 shown in FIG. 27.

Figure 28:
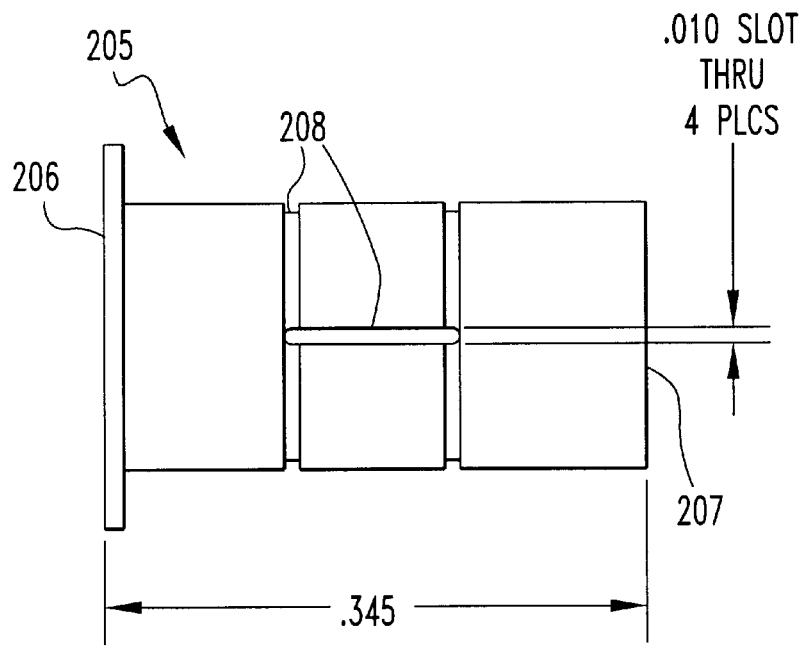
FIG. 28 is a schematic representation of a side view of a crimp grommet.
Figure 29:
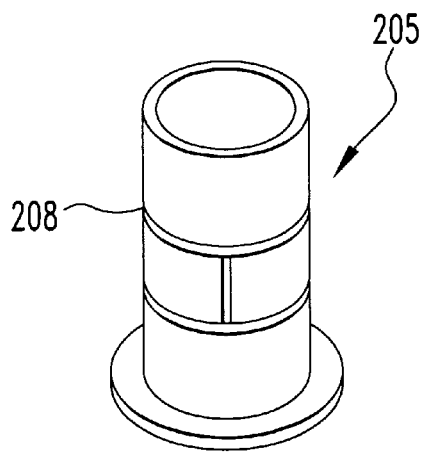
FIG. 29 is a schematic representation of a perspective view of an uncrimped crimp grommet.
Figure 30:
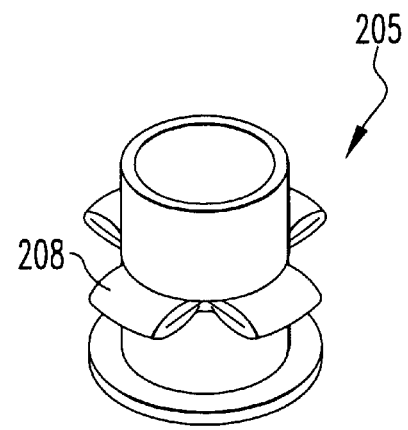
FIG. 30 is a schematic representation of a perspective view of a crimped crimp grommet.

In another embodiment of a grommet, there is shown in FIGS. 28, 29 and 30 a side view of a crimp grommet 205, perspective view of an uncrimped crimp grommet 205, and a crimped view of a crimp grommet 205. The crimp grommet 205 is inserted into a hole and then pliers grip the top 206 and bottom 207 of the uncrimped crimp grommet 205. The pliers are squeezed closed causing the crimp grommet to crimp along pre-cuts in the body of the crimp grommet.

Figure 31:
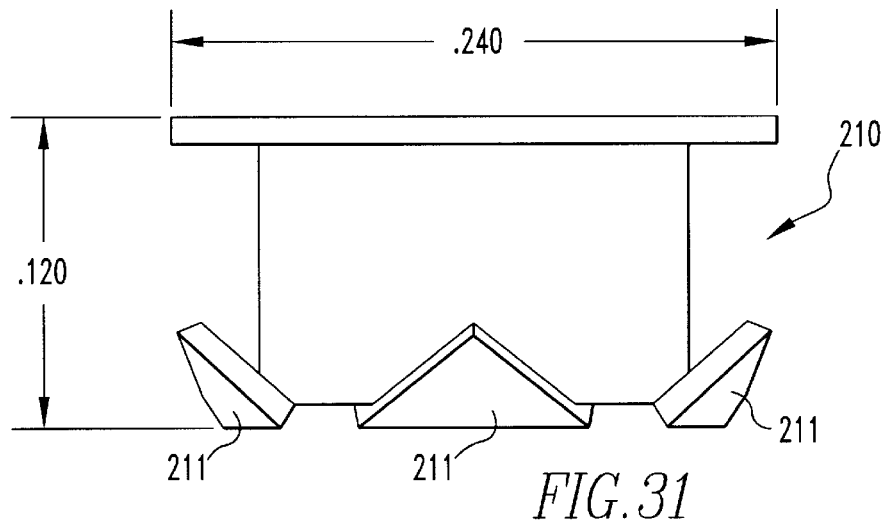
FIG. 31 is a schematic representation of a hook grommet.

FIG. 31 shows another embodiment of a grommet, a hook grommet 210. The hook grommet 210 is forced into a hole. Due to the hooks 211 angling up, the hook grommet 210 can move down, but if it is attempted to be moved up, the hooks 211 catch on the cartilage or hard tissue, preventing it from doing so.

Figures 32, 33:
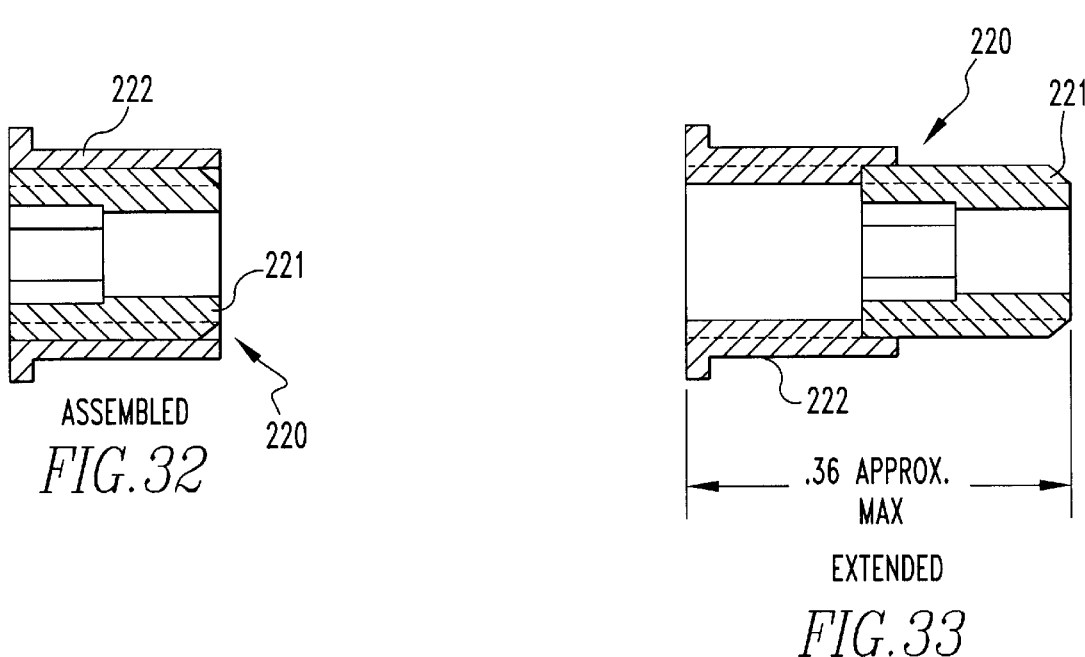
FIG. 32 is a schematic representation of a telescoping grommet which is not extended.
FIG. 33 is a schematic representation of a telescoping grommet which is extended.
Figure 34:
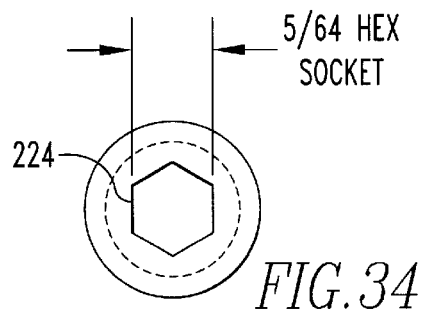
FIG. 34 is a schematic representation of a top view of a telescoping grommet.

FIGS. 32 and 33 show a telescoping grommet 220 made of a threaded male piece 221 inside a female piece 222 which is also threaded. The assembled male and female pieces are screwed into a hole by way of a hex socket 224 shown in FIG. 34, in the female piece 222 which extends beyond the male piece 221. A socket wrench disposed in the socket 224 is rotated until the female piece 222 is in place. Then the male piece 221 through its own hex socket is threaded through the female piece 222 to further extend it into the hard tissue, such as the sternum.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. A method of bringing together a first side of a sternum and a second side of the sternum comprising the steps of:

placing a stop mechanism under the first side of the sternum;

introducing an object into the first side of the sternum over where the stop mechanism is located so the object strikes the stop mechanism after it has passed through the first side of the sternum;

removing the object from the first side of the sternum so a hole remains in the sternum;

placing a first grommet in the hole;

placing a second grommet in a hole in the second side of the sternum;

introducing a wire suture into the first and second grommets;

drawing the ends of the wire suture which extend from the first and second grommets together so the first and second sides of the sternum come together; and crimping the ends of the wire suture.

* * * * *